United States Patent [19]

Saccarello

[11] Patent Number: 4,952,702
[45] Date of Patent: Aug. 28, 1990

[54] PROCESS FOR THE PREPARATION OF (1,4-DIARYL-PYRAZOL-3-YL)-ACETIC ACIDS

[75] Inventor: Luisa Saccarello, Milan, Italy

[73] Assignee: Seuref A.G., Vaduz, Liechtenstein

[21] Appl. No.: 376,398

[22] Filed: Jul. 6, 1989

[30] Foreign Application Priority Data

Jul. 8, 1988 [IT] Italy .................. 21301 A/88

[51] Int. Cl.$^5$ .................................. C07D 231/12
[52] U.S. Cl. .......................................... 548/378
[58] Field of Search ............................. 548/378

[56] References Cited

U.S. PATENT DOCUMENTS 4,042,706  8/1977  Ahrens et al. ................. 548/378

FOREIGN PATENT DOCUMENTS 40467  3/1982  Japan .

Primary Examiner—Robert W. Ramsuer
Attorney, Agent, or Firm—Bucknam and Archer

[57] ABSTRACT

(1,4-Diaryl-purazol-3-yl)-acetic acids of the formula

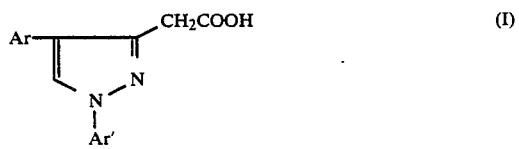

wherein Ar and Ar', which can be the same or different, represents a phenyl group optionally substituted with 1 or 3 halogen atoms, $C_1$–$C_4$ alkyl or $C_1$–$C_4$ alkoxy groups, are prepared by reacting β-styryl amines with compounds of formula ClCO-$CH_2$-A (wherein A represents a CN, COOR or $CONR^1R^2$ group, R being an alkyl, benzyl or benzohydryl group and $R^1$ and $R^2$ being H or an alkyl, benzyl or benzohydryl group).

5 Claims, No Drawings

PROCESS FOR THE PREPARATION OF (1,4-DIARYL-PYRAZOL-3-YL)-ACETIC ACIDS

The invention concerns a new process for the preparation of (1,4-diaryl-pyrazol-3-yl)-acetic acids of the formula I

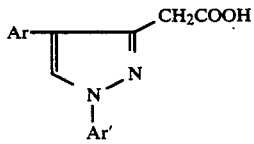   (I)

wherein Ar and Ar', which can be the same or different, represent a phenyl group, optionally substituted with 1-3 halogen atoms, $C_1-C_4$ alkyl groups or $C_1-C_4$ alkoxy groups.

The compound of formula I are endowed with a high antiinflammatory activity and some of them are of an effective therapeutical interest.

Processes are known for the preparation of, for instance, [1-(4-fluorophenyl)-4-(4-chlorophenyl)-1H-pyrazol-1-yl]acetic acid. According to EP No. 54,812, ethyl 2-chloro-2-(4-fluorophenylhydrazono)acetate is condensed with 4-(7-chloro-β-styryl)morpholine and the so obtained ethyl [1-(4-fluorophenyl)-4-(4-chlorophenyl)-1H-pyrazol-3-yl]-carboxylate is hydrolyzed to give the corresponding carboxylic acid, which is converted in the final product through the following steps: (a) reduction of —COOH to —CH₂OH with $HAl(C_4H_9)$; (b) reaction of the carbinol with concentrated HBr; (c) reaction of the —CH₂Br compound with potassium cyanide; (d) hydrolysis of the —CH₂CN compound with sodium hydroxyde.

It is clear that the above summarized process is quite unsuitable for an industrial production, inasmuch it is affected by a lot of disadvantages: the high number of steps, the low yield of some of them, the use of some very dangerous reagents, such as the potassium cyanide and, above all, the alkyl chloro-hydrazonoacetates, well known from the point of view of toxicity and allergic activity.

It has now been found that compounds of formula I may be easily obtained by reacting 4-(β-styryl) amines of formula II

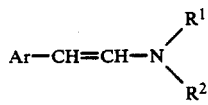   (II)

(wherein Ar is as above defined, whereas $R^1$ and $R^2$, which can be the same or different, represent $C_1-C_4$ alkyl group or, together with the N-atom, represent an heterocyclic group) with compounds of formula III

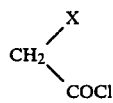   (III)

(wherein X represents a group selected from COOR, $CONR^3R^4$ and CN, whereas R is an alkyl group or a benzyl or benzohydryl group and $R^3$ and $R^4$, which can be the same or different, represent a hydrogen atom or an alkyl or a benzyl or benzohydryl group) to give intermediates of formula IV

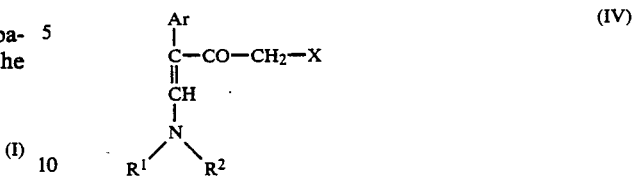   (IV)

(wherein Ar and X have the above mentioned meanings); and by condensing the enamine intermediates IV with an arylhydrazine of formula V

   (V)

(wherein Ar' has the above mentioned meaning) to give pyrazole derivatives of formula VI

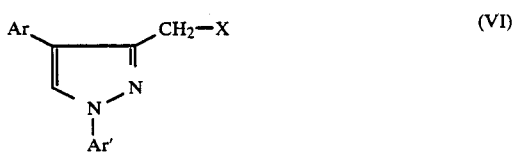   (VI)

(wherein Ar, Ar' and X are as above defined) which are finally hydrolyzed to the compounds of formula I. In the case that R is a benzyl or benzohydryl group, the conversion to I can be carried out by hydrogenolysis in the presence of palladium on charcoal or like catalysators. Preferably, in the formula II, $R^1$ and $R^2$ are methyl or ethyl groups or, more preferably, they represent, together with the N-atom, a morpholino, piperidino or pyrrolidino group.

Preferably, in the formula III, X represent a COOR, R being preferably a t-butyl group or a benzohydryl group. Alternatively, are preferred compounds of formula III with X=$NHR^3$, $R^3$ being preferably a t-butyl group or a benzohydryl group.

The reaction of the enamines II with the chlorocarbonyl compounds III is carried out in inert solvents and in the presence of a base, preferably a tertiary organic base (for instance triethylamine or pyridine) as acceptor of the hydrochloric acid which forms during the reaction, at temperatures ranging from 0° to 100° C.

At the end of the reaction it is not necessary to isolate the intermediate IV; the hydrochloride of the tertiary base is filtered and the filtered solution is directly reacted with the arylhydrazine, at a temperature ranging, too, from 0° and 100° C. Preferred solvents are $CH_2Cl_2$ or $CHCl_3$; a preferred temperature is the reflux temperature of the mixture. At the end of the ring closure (the reaction can be easily followed by TLC) the solvent is evaporated i.v. and the raw product is purified by crystallization.

According to the invention, compounds of formula I can be prepared in an easy way, without the use of toxic or dangerous reagents, in a otisfactory yield.

The following Examples are given only A SCOPO ILLUSTRATIVO. Esters and amides of chlorocarbonyl-acetic acid are easily obtained from the corresponding mono-esters and mono-amides of malonic acid by reaction with $PCl_5$ or $SOCl_2$.

EXAMPLE 1

[1-(4-Fluorophenyl)-4-(4-chlorophenyl)-1H-pyrazol-3-yl]-acetic acid

(a) Benzohydryl [1-(4-fluorophenyl)-4-(4-chlorophenyl)-1H-pyrazol-3-yl]-acetate To 1 g (4,5 mM) of 1-(4-chlorophenyl)-2-morpholinoethylene in 60 ml of CHCl$_3$, 1,30 g (4,5 mM) of benzohydryl chlorocarbonyl-acetate and 0,45 g (4,5 mM) of triethylamine are added. After the end of the reaction (~6 hours) the triethylammonium chloride is filtered and the solution is refluxed with 0,563 g (4,5 mM) of 4-fluorophenyl-hydrazine. The solvent is evaporated in vacuo and the raw product is crystallized from ethanol: needles, m.p. 172° C., TLC-unitary. Elemental analysis, IR- and $^1$H-NMR-specro are in agreement with the proposed structure.

(b) [1-(4-Fluorophenyl)-4-(4-chlorophenyl)-1H-pyrazol-3-yl]-acetic acid 1,49 Grams of the ester prepared according to (a) are stirred in 30 ml of trifluoroacetic acid, at room temperature. The hydrolysis is followed by TLC; at the end the excess of CF$_3$—COOH is evaporated in vacuo and the residue is crystallized from acetic acid/ethanol. The title product is identical with a sample prepared according to EP 54812.

EXAMPLE 2

[1-(4-Fluorophenyl)-4-(4-chlorophenyl)-1H-pyrazol-3-yl]-acetic acid

According to Example 1a, but using a corresponding amount of t-butyl chlorocarbonyl-acetate instead of the benzohydryl ester, the t-butyl ester of [1-(4-fluorophenyl)-4-(4-chlorophenyl)-1H-pyrazol-3-yl]-acetic acid is obtained, m.p. 143° C., IR- and $^1$H-NMR-spectra in agreement with the proposed structure.

The hydrolysis with CF$_3$—COOH leads to the title product. Overall yield (on 1-(4-chlorophenyl)-2-morpholino-ethylene): 72%.

EXAMPLE 3

[1-(4-Fluorophenyl)-4-(4-chlorophenyl)-1H-pyrazol-3-yl]-acetic acid 1,49 Grams (3 mM) of the benzohydryl [1-(4-fluorophenyl)-4-(4-chlorophenyl)-1H-pyrazol-3-yl]-acetate are dissolved in 40 ml of tetrahydroflurane. To the solution 0,4 g of Pd on charcoal (10%) are added, then the mixture is hydrogenated at room temperature and pressure. At the end of the reaction the catalysator is filtered, the solvent evaporated and the product crystallized from acetic acid/ethanol. The title product is obtained in almost quantitative yield.

EXAMPLE 4

[1-(4-Fluorophenyl)-4-(4-chlorophenyl)-1H-pyrazol-3-yl]-acetic acid 1-(4-Chlorophentyl)-2-pyrrolidino-ethylene is reacted with the N-benzylamide of chlorocarbonyl-acetic acid (molars ratio 1:1), in dioxane and in the presence of an equimolecular amount of triethylamine.

After removal of the triethylammonium chloride the raw solution is added with the calculated amount of 4-flurophenyl-hydrazine. The N-benzylamide of [1-(4-fluorophenyl)-4-(4-chlorophenyl)-1H-pyrazol-3-yl]-acetic acid is obtained in a yield of 78%, m.p. 138° C.

The hydrolysis of these amide with CF$_3$—COOH gives the title product; yield 89%.

I claim:

1. Process for the preparation of (1,4-diaryl-pyrazol-3-yl)-acetic acid of the formula I

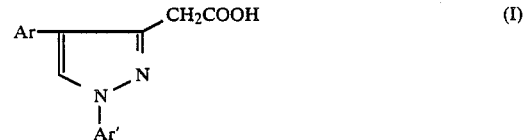

wherein Ar and Ar', which can be the same or different, represent a phenyl group, optionally substituted with 1-3 halogen atoms, C$_1$-C$_4$ alkyl groups or C$_1$-C$_4$ alkoxy groups, which process comprises:

reacting 4-($\beta$-styryl) amines of formula II

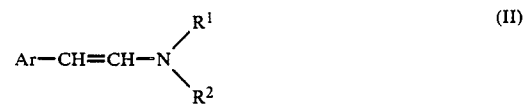

(wherein Ar is as above defined, whereas R$^1$ and R$^2$, which can be the same or different, represent C$_1$-C$_4$ alkyl group or, together with the N-atom, represent an heterocyclic group) with compounds of formula III

(wherein X represents a group selected from COOR, CONR$^3$R$^4$ and CN, whereas R is an alkyl group or a benzyl or benzohydryl group and R$^3$ and R$^4$, which can be the same or different, represent a hydrogen atom or an alkyl or a benzyl or benzohydryl group) to give intermediates of

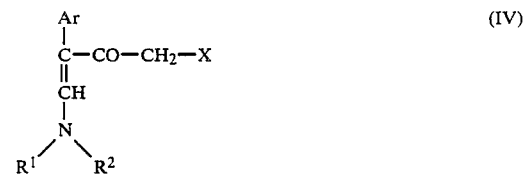

(wherein Ar and X have the above mentioned meanings); and condensing the enamine intermediates IV with an arylhydrazine of formula V

(wherein Ar' has the above mentioned meaning) to give pyrazole derivatives of formula VI.

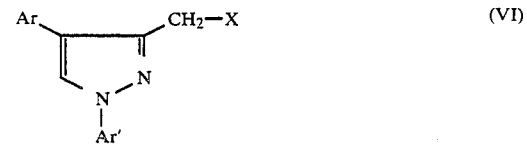

(wherein Ar, Ar' and X are as above defined) which are finally hydrolyzed to the compounds of formula I.

2. Process according to claim 1, wherein, in the compounds of formula II, $R^1$ and $R^2$ represent together with the N-atom, a morpholino group.

3. Process according to claim 1, wherein, in the compounds of formula III, X represents a t-butoxycarbonyl, benzohydryloxycarbonyl, t-butylaminocarbonyl or benzohydrylamino carbonyl group.

4. Process according to claim 1, wherein the reaction of the enamines II with the compounds III is carried out in an inert solvent and in the presence of a tertiary base.

5. Process according to claim 1, wherein, after removal of the tertiary base hydrochloride which forms in the reaction of the enamines II with the compounds III, the resulting solution is directly reacted with the arylhydrazine V, without isolation of the intermediate IV.

* * * * *